United States Patent [19]

Ceprini et al.

[11] 4,316,987
[45] Feb. 23, 1982

[54] PARTIAL (2,2,4-TRIMETHYLPENTANE-1,3-DIOL MONOISOBUTYRATE) ESTERS OF POLYCARBOXYLIC ACIDS AND WATER-SOLUBLE SALTS OF SAID PARTIAL ESTERS

[75] Inventors: Mario Q. Ceprini, Cedarhurst, N.Y.; Marvin Koral, Warren, N.J.

[73] Assignee: TennecoChemicals, Inc., Piscataway, N.J.

[21] Appl. No.: 223,875

[22] Filed: Jan. 9, 1981

[51] Int. Cl.³ .................. C07C 69/40; C07C 69/44; C07C 69/593; C07C 69/60
[52] U.S. Cl. .................. 560/199; 526/344; 526/345; 560/90
[58] Field of Search .................. 560/90, 199

[56] References Cited

U.S. PATENT DOCUMENTS

| | | | |
|---|---|---|---|
| 2,588,194 | 3/1952 | Arundale et al. | 560/199 |
| 2,703,811 | 3/1955 | Smith | 560/199 |
| 3,048,608 | 8/1962 | Girard et al. | 560/199 X |
| 3,318,835 | 5/1967 | Hagemeyer et al. | 560/199 X |
| 3,714,053 | 1/1973 | Mottez et al. | 560/85 |
| 4,014,708 | 3/1977 | Kaiser et al. | 560/90 |

Primary Examiner—Natalie Trousof
Assistant Examiner—Vera C. Clarke
Attorney, Agent, or Firm—Evelyn Berlow

[57] ABSTRACT

Partial (2,2,4-trimethylpentane-1,3-diol monoisobutyrate) esters of polycarboxylic acids and water-soluble salts of these esters are useful in the manufacture of vinyl halide resins that have excellent optical properties.

10 Claims, No Drawings

PARTIAL (2,2,4-TRIMETHYLPENTANE-1,3-DIOL MONOISOBUTYRATE) ESTERS OF POLYCARBOXYLIC ACIDS AND WATER-SOLUBLE SALTS OF SAID PARTIAL ESTERS

This invention relates to partial (2,2,4-trimethylpentane-1,3-diol monoisobutyrate) esters of polycarboxylic acids and to water-soluble salts of said partial esters. These compounds, which have the structural formula

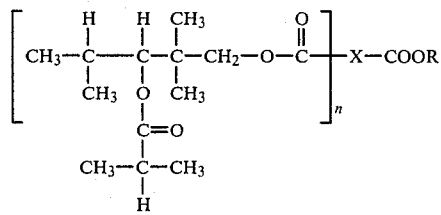

wherein X represents the residue of a polycarboxylic acid having 2 to 4 carboxyl groups and 4 to 20 carbon atoms, n is a number in the range of 1 to 3, and R represents hydrogen, ammonium, amine, or alkali metal, are useful in the manufacture of vinyl halide resins that have excellent optical properties.

Plastisols, which are dispersions of finely-divided vinyl halide resins in liquid plasticizers, are widely used as coatings for textiles, paper, flooring, wall coverings, metals, and other substrates. In addition, plastisol films may be used by themselves as finished articles, e.g., gloves and packaging materials. Because in these applications the plastisols are used not only to protect the substrates but also to decorate them or to enhance their appearance, the plastisol coatings and films must have a good appearance, that is, they must be clear and have high gloss.

In the commercial production of plastisols, surfactants are often used to lower the viscosity, to improve viscosity stability, and to improve the release of air from the compositions. When anionic surfactants are employed for these purposes, their presence in the finished plastisols causes clouding or hazing in films formed therefrom, which may be due to the incompatibility of the surfactant with other components of the plastisol compositions and/or to the presence of inorganic salts, which are commonly found in commercial surfactants.

In copending application U.S. Ser. No. 189,398, which was filed on Sept. 22, 1980 and which is incorporated herein by reference, Ceprini et al. disclosed that the optical properties of plastisol compositions that comprise vinyl chloride resins can be improved by incorporating in the compositions acid esters that are partial esters of polycarboxylic acids that have a free carboxyl group. These acid esters have the structural formula (R'OOC)$_n$—X—COOH wherein each R' represents the residue of an alcohol having 1 to 18 carbon atoms and X and n have the aforementioned significance. The groups represented by R' and by X may be saturated or unsaturated, aliphatic, cycloaliphatic, or aromatic groups; they may have alkyl, alkoxy, ester, halogen, or other substituents.

A preferred group of acid esters for use in the preparation of plastisol compositions from which clear, glossy coatings and films can be prepared are partial (2,2,4-trimethylpentane-1,3-diol monoisobutyrate) esters of polycarboxylic acids having 2 to 4 carboxyl groups and 4 to 20 carbon atoms that have the structural formula

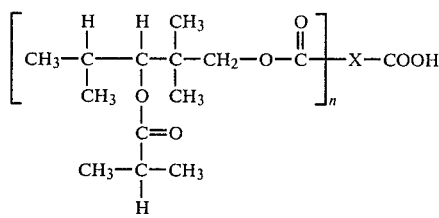

wherein X and n have the aforementioned significance.

The acid esters of this invention can be prepared by any suitable and convenient procedure. For example, they can be prepared by the direct esterification of 2,2,4-trimethylpentane-1,3-diol monoisobutyrate with a polycarboxylic acid or anhydride in an amount that will yield an ester having a free carboxyl group. The esterification may be carried out in the absence of a solvent or in the presence of an organic solvent, such as toluene. If desired, an esterification catalyst, for example, stannous oxide, p-toluenesulfonic acid, or tetrabutyl titanate, can be used. The acid esters prepared in this way may contain minor amounts of unreacted alcohol, unreacted carboxylic acid or anhydride, and/or esters in which all of the carboxyl groups of the acid have been esterified.

The following are illustrative of the polycarboxylic acids that can be used in the preparation of the acid esters of this invention: succinic acid, glutaric acid, adipic acid, azelaic acid, sebacic acid, dodecenylsuccinic acid, brassilic acid, maleic acid, fumaric acid, citraconic acid, itaconic acid, glutaconic acid, tricarballylic acid, phthalic acids, trimellitic acid, trimesic acid, pyromellitic acid, and mixtures thereof. The acid esters are preferably prepared from 2,2,4-trimethylpentane-1,3-diol monoisobutyrate and an aliphatic or aromatic dicarboxylic acid, such as maleic acid, succinic acid, adipic acid, dodecenylsuccinic acid, and phthalic acids or the anhydride of these acids.

The amount of the acid esters of this invention that is incorporated in the plastisol compositions is that which will yield plastisols from which clear, glossy coatings and films can be prepared. In most cases, from 1 part to 20 parts by weight of an acid ester is added per 100 parts by weight of vinyl halide resin in the composition. Compositions having the best combinations of clarity, gloss, and other properties result when from 2 parts to 6 parts of acid ester is used per 100 parts by weight of vinyl halide resin in the composition.

The plastisol compositions into which the acid esters are incorporated comprise a vinyl halide resin and at least one plasticizer. The vinyl halide resins that may be used in the preparation of the plastisol compositions are prepared by the emulsion polymerization of a vinyl halide, usually vinyl chloride, alone or in the presence of up to 30% of an ethylenically-unsaturated comonomer, such as vinyl acetate, vinyl propionate, vinyl butyrate, vinylidene chloride, ethylene, ethyl acrylate, and the like.

The vinyl halide resin is preferably polyvinyl chloride. Any of the well-known plasticizers for vinyl halide resins can be used in the preparation of the plastisol compositions. These include dibutyl phthalate, dioctyl phthalate, butyl lauryl phthalate, butyl benzyl phthalate, dibutyl sebacate, dioctyl adipate, tricresyl phosphate, octyl diphenyl phosphate, 2,2,4-trimethylpentane-1,3-diol monoisobutyrate monobenzoate, and dipropylene glycol dibenzoate. The plastisol compositions may also contain heat and light stabilizers, pigments, dyes, fillers, extenders, defoamers, and other additives in the amounts ordinarily used for the purposes indicated.

The plastisol compositions into which the acid esters of this invention are incorporated are prepared by blending the ingredients at a temperature in the range of 40° to 150° C. until a uniform composition is obtained. The acid esters may be added directly to the other ingredients of the compositions, or they may be added as a blend with the plasticizer.

Ceprini et al. disclosed in copending application U.S. Ser. No. 196,948, which was filed on Oct. 14, 1980 and which is incorporated herein by reference, that water-soluble salts of acid esters that are partial (2,2,4-trimethylpentane-1,3-diol monoisobutyrate) esters of polycarboxylic acids are excellent emulsifying agents for the polymerization of a monomer component that comprises vinyl chloride. The use of these acid ester salts as the emulsifying agent in the production of vinyl chloride polymers improves the optical properties of coatings and films that contain these polymers without adversely affecting their thermal stability, resistance to water, to acids, to alkali, and to organic chemicals, and other desirable properties.

The water-soluble salts that can be used as emulsifying agents in the polymerization of vinyl chloride include the ammonium, amine, and alkali metal salts of partial (2,2,4-trimethylpentane-1,3-diol monoisobutyrate) esters of polycarboxylic acids having 2 to 4 carboxyl groups and 4 to 20 carbon atoms.

These water-soluble salts are readily prepared by mixing substantially equivalent amounts of an acid ester and a basic compound with sufficient water to produce an aqueous solution of a water-soluble salt of the acid ester. An excess of the basic compound may be used to bring the aqueous solution to a pH in the range of 7.5 to 10, preferably 8 to 9. Among the basic compounds that can be used to form the water-soluble salts are sodium hydroxide, potassium hydroxide, lithium hydroxide, ammonium hydroxide, triethylamine, diethanolamine, triethanolamine, dimethylaminoethanol, N-methyldiethanolamine, diisopropanolamine, ethylene diamine, 2-amino-2-methylpropanol, hexamethylenetetramine, pyridine, morpholine, and the like.

When the acid ester salt solution is to be used as the emulsifying agent in a vinyl chloride polymerization process, it is generally preferred that it contain 20% to 60% by weight of the acid ester salt, with particularly good results being obtained when the emulsifying agent is an aqueous solution that contains from 35% to 50% by weight of the water-soluble acid ester salt.

The amount of the acid ester salt that is used as the emulsifying agent in the preparation of vinyl chloride polymers is usually in the range of from 1% to 5% by weight, preferably 1.5% to 3% by weight, based on the weight of the monomer component in the reaction mixture.

The acid ester salts of this invention can be used as the emulsifying agent in convention emulsion, dispersion, or suspension procedures for the production of vinyl chloride polymers. In the emulsion polymerization processes, vinyl chloride polymers are prepared using such water-soluble initiators as hydrogen peroxide, organic peroxides, potassium persulfate, and redox systems at a temperature in the range of 40° C. to 80° C. In the suspension and dispersion procedures, the polymerization initiator, which is monomer-soluble, may be an organic peroxide, an alkyl peroxydicarbonate, an alkyl peroxypivalate, an azo compound such as azobisisobutyronitrile, or a mixture thereof.

The acid salts can be used as the emulsifying agent in the production of vinyl chloride homopolymers as well as polymers formed by the copolymerization of vinyl chloride with a water-soluble ethylenically-unsaturated monomer that is copolymerizable therewith. Suitable comonomers include vinyl acetate, vinyl propionate, vinyl stearate, vinyl benzoate, ethylene, propylene, methyl methacrylate, ethyl acrylate, allyl acrylate, acrylamide, acrylonitrile, methacrylonitrile, vinylidene chloride, vinyl ethers, dialkyl fumarates and maleates, and the like. When one or more of the aforementioned comonomers are used, the monomer component contains at least 70% by weight of the vinyl chloride; it preferably contains 80% to 90% by weight of vinyl chloride and 10% to 20% by weight of vinyl acetate.

The invention is further illustrated by the examples that follow.

EXAMPLE 1

A mixture of 653 grams (3.0 moles) of 2,2,4-trimethylpentane-1,3-diol monoisobutyrate (Eastman's Texanol) and 406.4 grams (2.7 moles) of phthalic anhydride was sparged with nitrogen and heated at 140°-145° C. for 1-2 hours and then cooled to room temperature. The mono(2,2,4-trimethylpentane-1,3-diol monoisobutyrate) phthalate obtained was a clear liquid that had an acid number of 146 (calculated, 145).

EXAMPLES 2-4

Following the procedure of Example 1, except that esterification temperatures in the range of 140°-180° C. were used, a series of mono(2,2,4-trimethylpentane-1,3-diol monoisobutyrate) esters of aliphatic dicarboxylic acids was prepared. The acids and the amounts of the reactants that were used and the acid numbers of the acid esters are shown in Table I.

TABLE I

| | Mono(2,2,4-Trimethylpentane-1,3-diol monoisobutyrate) Esters of Aliphatic Dicarboxylic Acids | | | | | | |
|---|---|---|---|---|---|---|---|
| | Amount of 2,2,4-Trimethylpentane-1,3-diol monoisobutyrate Used | | | Acid Used | | Acid Number of Ester | |
| Ex. No. | Grams | Moles | | Grams | Moles | Found | Calcd |
| 2 | 756.8 | 3.50 | Maleic anhydride | 312 | 3.18 | 175 | 167 |

TABLE I-continued

Mono(2,2,4-Trimethylpentane-1,3-diol monoisobutyrate) Esters of Aliphatic Dicarboxylic Acids

| Ex. No. | Amount of 2,2,4-Trimethylpentane-1,3-diol monoiso-butyrate Used Grams | Moles | Acid Used | Grams | Moles | Acid Number of Ester Found | Calcd |
|---|---|---|---|---|---|---|---|
| 3 | 297.2 | 1.375 | Dodecenyl-succinic anhydride | 329.8 | 1.25 | 114 | 112 |
| 4 | 376.1 | 1.74 | Succinic anhydride | 158.1 | 1.58 | 171 | 166 |

EXAMPLE 5

A reaction mixture that contained 345.5 grams (1.60 moles) of 2,2,4-trimethylpentane-1,3-diol monoisobutyrate, 212.1 grams (1.45 moles) of adipic acid, 40 grams of toluene, and 1.0 gram of stannous oxide was stirred, sparged with nitrogen, and heated at its reflux temperature (189°–221° C.) until 23.4 grams of water had been evolved. The reaction mixture was heated at 170° C./40–50 mm Hg absolute to remove toluene and water from it and then cooled to room temperature. The acid ester of adipic acid that was obtained had an acid number of 141 (calculated, 153).

EXAMPLE 6

The composition of the products of Examples 1–5 was determined by gas chromatographic analyses. The results obtained are summarized in Table III.

TABLE II

Composition of Acid Esters of Examples 1–5

| Product of Example | Ester | Components (%) Mono Ester | Di Ester |
|---|---|---|---|
| 1 | Mono(2,2,4-trimethylpentane-1,3-diol monoisobutyrate) phthalate | 83.2 | 0.9 |
| 2 | Mono(2,2,4-trimethylpentane-1,3-diol monoisobutyrate) maleate | 79.7 | 4.7 |
| 3 | Mono(2,2,4-trimethylpentane-1,3-diol monoisobutyrate) dodecenylsuccinate | 94.1 | — |
| 4 | Mono(2,2,4-trimethylpentane-1,3-diol monoisobutyrate) succinate | 83.1 | 5.4 |
| 5 | Mono(2,2,4-trimethylpentane-1,3-diol monoisobutyrate) adipate | 48.0 | 36.0 |

EXAMPLE 7

Resinous compositions were prepared by mixing the following materials together in a Henschel mixer at a temperature in the range of 60° C. to 90° C. until a uniform composition was obtained:

| | Parts by Weight |
|---|---|
| PVC Dispersion Resin (Tenneco 1742) | 100 |
| 2,2,4-Trimethylpentane-1,3-diol monoisobutyrate monobenzoate (Tenneco Nuoplaz 1046) | 52* |
| Epoxidized Soybean Oil | 4 |
| Liquid Calcium/Zinc Stabilizer (Tenneco V-1420) | 4 |
| Acid Ester (Product of Ex. 1 or Ex. 2) | 3 |

*Comparative Example A, which contained no acid ester, contained 55 parts by weight of this component.

Films 10 mils thick and about 4"×6" were drawn down on glass by means of a Bird Applicator. The films were fused at 204° C. for either 6 minutes or 8 minutes. The gloss of the films was determined using a Gardner 60° Precision Gloss Meter, GG 9100 Series. The haze measurements were made using a Gardner Pivotable-Sphere Haze Meter, HG 1204. The results obtained are summarized in Table III.

TABLE III

Properties of PVC Plastisol Compositions Containing Acid Esters

| | 60° Gloss | | % Haze | |
|---|---|---|---|---|
| Partial Ester Used | Fused for 6 Min. | Fused for 8 Min. | Fused for 6 Min. | Fused for 8 Min. |
| Product of Ex. 1 | 106 | 120 | 7.0 | 4.9 |
| Product of Ex. 2 | 109 | 118 | 7.6 | 5.6 |
| None (Comp. Ex. A) | 88 | 98 | 15.7 | 11.0 |

EXAMPLE 8

Resinous compositions were prepared by mixing the following materials together in a Henschel mixer at a temperature in the range of 60° C. to 90° C. until a uniform composition was obtained:

| | Parts by Weight |
|---|---|
| PVC Dispersion Resin (Tenneco 1742) | 100.0 |
| Dioctyl Phthalate | 23.7 |
| Butyl Benzyl Phthalate | 14.2 |
| 2,2,5-Trimethylpentane-1,3-diol diisobutyrate | 9.5 |
| Epoxidized Soybean Oil | 3.8 |
| Liquid Calcium/Zinc Stabilizer (Tenneco V-1420) | 3.8 |
| Acid Ester (Product of Ex. 3, Ex. 4, or Ex. 5) | 3.0 |
| Comparative Examples B–D, which contained no acid ester, contained an additional 3.0 parts by weight of the plasticizer mixture. | |

Films 10 mils thick and about 4"×6" were drawn down on glass by means of a Bird Applicator. The films were fused at 204° C. for either 5 minutes or 7 minutes and evaluated by the procedures described in Example 7. The results obtained are summarized in Table IV. These evaluations were performed over a period of time using different and freshly-prepared controls for each test.

TABLE IV

Properties of PVC Plastisol Compositions Containing Acid Esters

| Acid Ester Used | 60° Gloss | | % Haze | |
|---|---|---|---|---|
| | Fused for 5 Min. | Fused for 7 Min. | Fused for 5 Min. | Fused for 7 Min. |
| Product of Ex. 3 | — | — | 10.4 | 6.3 |
| None (Comp. Ex. B) | | | 20.5 | 16.9 |
| Product of Ex. 4 | 120 | 123 | 5.9 | 5.1 |
| None (Comp. Ex. C) | 102 | 115 | 17.0 | 12.5 |
| Product of Ex. 5 | 92 | 120 | 11.3 | 5.8 |
| None (Comp. Ex. D) | 85 | 113 | 15.0 | 11.9 |

From the data in Tables III and IV, it will be seen that the incorporation of acid esters in PVC plastisol compositions significantly improved the clarity and gloss of films prepared from these compositions. In each case, the rheology, stability, and other properties of the compositions that contained acid esters were equivalent to those of the control compositions that did not contain acid esters.

EXAMPLE 9

To 16.2 grams (0.267 mole) of concentrated ammonium hydroxide and 174.2 grams of water was added 100 grams (0.267 mole) of the product of Example 1. The mixture was agitated for several minutes at room temperature to produce a 40% aqueous solution of the ammonium salt of mono(2,2,4-trimethylpentane-1,3-diol monoisobutyrate) phthalate. Additional ammonium hydroxide was added to the solution to raise its pH to 8.

EXAMPLES 10 and 11

Using the procedure described in Example 9 except that sodium hydroxide was used in place of ammonium hydroxide, solutions of the sodium salts of the products of Examples 1 and 2 were prepared.

EXAMPLES 12 to 15

Using the procedure described in Example 9 except that other acid esters were used in place of mono(2,2,4-trimethylpentane-1,3-diol monoisobutyrate) phthalate, the following salts were prepared.

| Ex. No. | Salt |
|---|---|
| 12 | Ammonium salt of mono(2,2,4-trimethylpentane-1,3-diol monoisobutyrate) maleate |
| 13 | Ammonium salt of mono(2,2,4-trimethylpentane-1,3-diol monoisobutyrate) dodecenylsuccinate |
| 14 | Ammonium salt of mono(2,2,4-trimethylpentane-1,3-diol monoisobutyrate) adipate |
| 15 | Ammonium salt of mono(2,2,4-trimethylpentane-1,3-diol monoisobutyrate) itaconate |

EXAMPLE 16

A series of polymerizations was carried out at 53.3° C. for 24 hours using a polymerization mixture that contained 103 parts of demineralized water, 100 parts of vinyl chloride, 2.62 parts of triallyl cyanurate as a 2% aqueous solution, 0.10 part of lauroyl peroxide, 0.05 part of di-2-ethylhexyl peroxydicarbonate, and various amounts of a 40% aqueous solution of an emulsifying agent that was either a water-soluble salt of a mono(2,2,4-trimethylpentane-1,3-diol monoisobutyrate) ester of a polycarboxylic acid or a comparative emulsifying agent. At the end of the polymerizations, the polymers were isolated and dried in a forced-air oven at 40° C.

The emulsifying agents and the amounts of each that were used are shown in Table V.

TABLE V

| Ex. No. | Emulsifying Agent | Amount of Emulsifying Agent Used (parts per 100 parts of vinyl chloride) |
|---|---|---|
| 16A | Product of Ex. 9 | 3.0 |
| 16B | Product of Ex. 9 | 1.8 |
| 16C | Product of Ex. 10 | 3.0 |
| 16D | Product of Ex. 11 | 3.0 |
| 16E | Product of Ex. 12 | 3.0 |
| 16F | Product of Ex. 12 | 1.8 |
| 16G | Product of Ex. 13 | 3.0 |
| 16H | Product of Ex. 14 | 3.0 |
| 16I | Product of Ex. 15 | 3.0 |
| Comp. Ex. E | Ammonium dihydroxystearate | 3.0 |
| Comp. Ex. F | Ammonium laurate | 3.0 |

EXAMPLE 17

Each of the PVC dispersion resins whose preparation is disclosed in Example 16 was used in the preparation of resinous compositions. These compositions were prepared by milling the following materials together at 138° C. for 5 minutes:

| | Parts |
|---|---|
| PVC Dispersion Resin | 100 |
| Dioctyl phthalate | 25 |
| Butyl benzyl phthalate | 15 |
| 2,2,4-Trimethylpentane-1,3-diol diisobutyrate | 10 |
| Epoxidized Soybean Oil | 4 |
| Liquid Calcium/Zinc Stabilizer (Tenneco V-1420) | 4 |

The compositions were pressed at 178° C. for 3 minutes to form 75 mil plaques. The clarity of the plaques was determined using a Gardner Pivotable-sphere Haze Meter, HG 1204 and a Gardner Digital Photometric Unit, PG-5500. The results obtained are summarized in Table VI.

TABLE VI

Clarity of PVC Plastisol Compositions

| Ex. No. | PVC Dispersion Resin Used in Preparation of the Plastisol Composition | % Haze |
|---|---|---|
| 17A | Product of Ex. 16A | 8.2 |
| 17B | Product of Ex. 16B | 2.8 |
| 17C | Product of Ex. 16C | 8.1 |
| 17D | Product of Ex. 16D | 9.6 |
| 17E | Product of Ex. 16E | 10.8 |
| 17F | Product of Ex. 16F | 8.4 |
| 17G | Product of Ex. 16G | 11.6 |
| 17H | Product of Ex. 16H | 7.0 |
| 17I | Product of Ex. 16I | 11.0 |
| Comp. Ex. G | Product of Comp. Ex. E | 18.6 |
| Comp. Ex. H | Product of Comp. Ex. F | 15.1 |

The data in Table VI show that the clarity of the PVC resin compositions was improved when the polymers used in their preparation were prepared using as emulsifying agent a water-soluble salt of a mono(2,2,4-trimethylpentane-1,3-diol monoisobutyrate) ester of a polycarboxylic acid. Films of the products of Examples 17A–17I also had higher gloss than those of Comparative Examples G and H, which contained PVC prepared with other emulsifying agents.

What is claimed is:

1. A compound having the structural formula

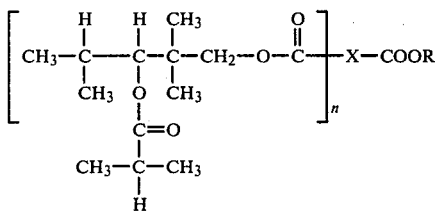

wherein X represents the residue of an aliphatic polycarboxylic acid having 2 to 4 carboxyl groups and 4 to 20 carbon atoms, n is a number in the range of 1 to 3, and R represents hydrogen, ammonium, amine, or alkali metal.

2. A compound as defined in claim 1 that is a mono(2,2,4-trimethylpentane-1,3-diol monoisobutyrate) ester of an aliphatic dicarboxylic acid.

3. The compound as defined in claim 2 that is mono(2,2,4-trimethylpentane-1,3-diol monoisobutyrate) maleate.

4. The compound as defined in claim 2 that is mono(2,2,4-trimethylpentane-1,3-diol monoisobutyrate) adipate.

5. A compound as defined in claim 1 that is the ammonium salt of a mono(2,2,4-trimethylpentane-1,3-diol monoisobutyrate) ester of an aliphatic dicarboxylic acid.

6. The compound as defined in claim 5 that is the ammonium salt of mono(2,2,4-trimethylpentane-1,3-diol monoisobutyrate) maleate.

7. A compound as defined in claim 1 that is the sodium salt of a mono(2,2,4-trimethylpentane-1,3-diol monoisobutyrate) ester of an aliphatic dicarboxylic acid.

8. A compound as defined in claim 2 that is mono(2,2,4-trimethylpentane-1,3-diol monoisobutyrate)-dodecenylsuccinate.

9. A compound as defined in claim 2 that is mono(2,2,4-trimethylpentane-1,3-diol monoisobutyrate) succinate.

10. A compound as defined in claim 5 that is the ammonium salt of mono(2,2,4-trimethylpentane-1,3-diol monoisobutyrate) itaconate.

* * * * *